(12) United States Patent
Kim et al.

(10) Patent No.: US 12,297,242 B2
(45) Date of Patent: May 13, 2025

(54) COMPOSITION FOR PREVENTING OR TREATING PARKINSON'S DISEASE, COMPRISING AEG-1 S298D AS ACTIVE INGREDIENT

(71) Applicant: KYUNGPOOK NATIONAL UNIVERSITY INDUSTRY-ACADEMIC COOPERATION FOUNDATION, Daegu (KR)

(72) Inventors: Sang Ryong Kim, Daegu (KR); Minsang Shin, Daegu (KR); Eunju Leem, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 913 days.

(21) Appl. No.: 17/291,616

(22) PCT Filed: Oct. 10, 2019

(86) PCT No.: PCT/KR2019/013284
§ 371 (c)(1),
(2) Date: May 6, 2021

(87) PCT Pub. No.: WO2020/111501
PCT Pub. Date: Jun. 4, 2020

(65) Prior Publication Data
US 2022/0017582 A1 Jan. 20, 2022

(30) Foreign Application Priority Data
Nov. 28, 2018 (KR) .................. 10-2018-0149639

(51) Int. Cl.
*C07K 14/47* (2006.01)
*A23L 33/18* (2016.01)
(Continued)

(52) U.S. Cl.
CPC .......... *C07K 14/4702* (2013.01); *A23L 33/18* (2016.08); *C12N 15/86* (2013.01); *A61K 38/00* (2013.01)

(58) Field of Classification Search
CPC ......... A23L 33/18; A61K 38/00; A61K 31/48; A61K 38/16; A61K 38/17; A61K 38/18;
(Continued)

(56) References Cited

U.S. PATENT DOCUMENTS 7,517,973 B2 * 4/2009 Fisher .................... C07K 14/47
435/320.1

FOREIGN PATENT DOCUMENTS

KR 20150135867 A * 12/2015 ............. A61K 31/48
KR 10-1639198 B1 7/2016
KR 10-2018-0082084 A 7/2018

OTHER PUBLICATIONS

Krishnan et al., Quantitative analysis of the TNF-α-induced hosphoproteome reveals AEG-1/MTDH/LYRIC as an IKKβ substrate. Nat Commun 6, 6658 (2015), 1-15 and 13 pages of Supplemental. https://doi.org/10.1038/ncomms7658 (published online Apr. 7, 2015) (Year: 2015).*
(Continued)

*Primary Examiner* — Randall L Beane
(74) *Attorney, Agent, or Firm* — Revolution IP, PLLC (57) ABSTRACT

The present invention relates to a composition for preventing or treating Parkinson's disease comprising AEG-1 (S298D) as an active ingredient, and in the present invention, a point mutation was introduced into AEG-1 to induce a constitutively active form of AEG-1 (S298D), to construct
(Continued)

AAV-AEG-1 (S298D), and to apply an animal model for Parkinson's disease, and accordingly, it was confirmed that it exhibits a protective effect on brain tissue by preserving dopaminergic neurons and dopamine nerve fibers and thus AEG-1 is useful as a composition for preventing or treating Parkinson's disease, a health food composition for preventing or improving Parkinson's disease, etc.

**2 Claims, 4 Drawing Sheets
(2 of 4 Drawing Sheet(s) Filed in Color)**

Specification includes a Sequence Listing.

(51) Int. Cl.
*A61K 38/00* (2006.01)
*C12N 15/86* (2006.01)

(58) Field of Classification Search
CPC .. A61K 48/00; A61K 48/005; A61K 48/0075; A23V 2002/00; A23V 2200/322; A61P 25/16; C07K 14/4702; C07K 14/705; C12N 15/86; C12N 2750/14141; C12N 2750/14143; A01K 2207/20; A01K 2227/105; A01K 2267/0318
See application file for complete search history.

(56) References Cited

OTHER PUBLICATIONS

Segura-Aguilar, Can we conclude a potential therapeutic action for Parkinson's disease by using postmortem tissue and a preclinical model based on an exogenous neurotoxin?. Cell Death Dis 9, 748 (2018). https://doi.org/10.1038/s41419-018-0798-0 (Year: 2018).*
Han, Parkinson's disease early signs and causes, MedicalNewsToday, 9 pages (Jan. 24, 2024), also available at https://www.medicalnewstoday.com/articles/323396 (last visited Apr. 22, 2024) (Year: 2024).*
Pearlman et al., A mechanism for the evolution of phosphorylation sites. Cell. Nov. 11, 2011;147(4):934-46. doi: 10.1016/j.cell.2011.08.052. PMID: 22078888; PMCID: PMC3220604 (Year: 2011).*
Gustafsson et al., Codon bias and heterologous protein expression. Trends Biotechnol. Jul. 2004;22(7):346-53. doi: 10.1016/j.tibtech.2004.04.006. PMID: 15245907 (Year: 2004).*
Machine Translation of KR20150135867A , EPO Machine Translation of KR20150135867A, 57 pages, translated on Apr. 22, 2024 (Year: 2024).*
Leem et al., Upregulation of neuronal astrocyte elevated gene-1 protects nigral dopaminergic neurons in vivo. Cell Death Dis. May 1, 2018;9(5):449. doi: 10.1038/s41419-018-0491-3. PMID: 29670079; PMCID: PMC5906475I (published Apr. 18, 2018) (Year: 2018).*
Léger et al. (Conversion of serine to aspartate imitates phosphorylation-induced changes in the structure and function of microtubule-associated protein tau. J Biol Chem. Mar. 28, 1997;272(13):8441-6. doi: 10.1074/jbc.272.13.8441. PMID: 9079670 (Year: 1997).*
International Search Report for PCT/KR2019/013284 mailed Feb. 7, 2020 from Korean Intellectual Property Office.
Krishnan, R. K. et al., "Quantitative analysis of the TNF-α-induced phosphoproteome reveals AEG-1/MTDH/LYRIC as an IKKβ substrate", Nature Communications, 2015, vol. 6, thesis No. 6658, pp. 1-15.
Noch, E. et al., "The role of AEG-1/MTDH/LYRIC in the pathogenesis of central nervous system disease", Advances in cancer research, 2013, vol. 120, pp. 159-192, NIH Public Access Author Manuscript Version, internal pp. 1-27.
Leem, E. et al., "Upregulation of neuronal astrocyte elevated gene-1 protects nigral dopaminergic neurons in vivo", Cell death & disease, Apr. 18, 2018, vol. 9, thesis No. 449, pp. 1-15.
Paxinos and Watson, "The Rat Brain in stereotaxic coordinates", Fourth Edition, 1998.
Kim, S. R. et al., "Dopaminergic Pathway Reconstruction by Akt/Rheb-Induced Axon Regeneration", American Neurological Association, 2011, vol. 70, No. 1, pp. 110-120.
Kim, S. R. et al., "AAV Transduction of Dopamine Neurons With Constitutively Active Rheb Protects From Neurodegeneration and Mediates Axon Regrowth", Molecular Therapy, 2012, vol. 20, No. 2, pp. 275-286.
Kim, B-. W. et al., "Pathogenic Upregulation of Glial Lipocalin-2 in the Parkinsonian Dopaminergic System", The Journal of Neuroscience, May 18, 2016 • 36(20):5608-5622.
Won, S-. Y. et al., "Nigral dopaminergic PAK4 prevents neurodegeneration in rat models of Parkinson's disease", Science Translational Medicine Nov. 30, 2016: vol. 8, Issue 367, pp. 367ra170.

* cited by examiner

COMPOSITION FOR PREVENTING OR TREATING PARKINSON'S DISEASE, COMPRISING AEG-1 S298D AS ACTIVE INGREDIENT

CROSS REFERENCE TO PRIOR APPLICATIONS

This application is the 35 U.S.C. 371 national stage of International application PCT/KR2019/013284 filed on Oct. 10, 2019; which claims priority to Korean Patent Application No. 10-2018-0149639 filed on Nov. 28, 2018. The entire contents of each of the above-identified applications are hereby incorporated by reference.

TECHNICAL FIELD

The present invention relates to a composition for preventing or treating Parkinson's disease comprising AEG-1 (astrocyte elevated gene-1) (S298D) as an active ingredient.

BACKGROUND ART

Parkinson's disease (PD), along with Alzheimer's dementia, is one of the representative neurodegenerative diseases that occur in old age and it is known that about 1% of the 65-year-old population develops and the incidence rate increases with age. The symptoms of Parkinson's disease are motor disorders, such as tremor, rigidity, bradykinesia, and postural instability at rest. In addition, Parkinson's disease is characterized by microgliosis, astrogliosis, progressive degeneration of dopaminergic neurons, the presence of Lewy bodies in dopaminergic neurons and the accumulation of α-synuclein in the substantia nigra pars compacta.

The exact cause of Parkinson's disease is not yet clearly known, but environmental factors caused by neurotoxins such as pesticides, genetic factors, mitochondrial dysfunction and aging are known to be related. Genetic factors are known to be associated with gene mutations such as alpha-synuclein, Parkin, PINK-1, UCH-L1, and DJ-1. Currently, there are many drugs that alleviate the symptoms of Parkinson's disease, but drugs that can prevent the progression of the disease have not yet been reported, and the chronic use of the drug has a high risk of causing side effects that weaken the mind and body.

Drugs for the treatment of Parkinson's disease include L-dopa formulation, dopamine receptor agonists, anticholinergic drugs, Eldepryl and the like. However, most of these drugs are not causative treatments, but play a role in controlling symptoms, and thus require continuous administration of drugs. Long-term administration of these drugs causes a problem of drug side effects. For example, anticholinergic drugs may have autonomic nervous system abnormalities or mental function abnormalities, so there is a limit to continuous administration of them to elderly patients. In addition, in the case of L-dopa formulation, the effect gradually decreases with long-term administration, and Side effects such as distortion of the body or abnormal movements of the hands and feet moving by themselves occur. Furthermore, surgical treatment such as nerve stimulation using high frequency, that is, high frequency thalamotomy or deep brain stimulation, is also being performed, but there is a problem that invasive surgery is required and a lot of cost is consumed.

Therefore, since the etiology of Parkinson's disease is not accurately known, treatment methods are mainly used to improve symptoms rather than a fundamental treatment. There is an urgent need to develop a new and more effective therapeutic agent in order to prevent and treat Parkinson's disease.

DISCLOSURE

Technical Problem

An object of the present invention is to provide an AEG-1 S298D mutant protein, a gene encoding the same and an expression vector comprising the gene.

Another object of the present invention is to provide a pharmaceutical composition for preventing or treating Parkinson's disease.

Another object of the present invention is to provide a health food composition for preventing or improving Parkinson's disease.

Technical Solution

In order to achieve the above object, the present invention provides AEG-1 S298D mutation protein represented by SEQ ID NO: 1 in which 298th serine (S) from N-terminus in full amino acid sequence of AEG-1 (astrocyte elevated gene-1) protein is substituted by aspartic acid (D).

Also, the present invention provides a gene encoding the AEG-1 S298D mutant protein.

In addition, the present invention provides an expression vector comprising the gene.

Furthermore, the present invention provides a pharmaceutical composition for preventing or treating Parkinson's disease comprising the protein, the gene or the expression vector as an active ingredient.

In addition, the present invention provides a health food composition for preventing or improving Parkinson's disease comprising the protein, the gene, or the expression vector as an active ingredient.

Advantageous Effects

In the present invention, a point mutation was introduced into AEG-1 to induce a constitutively active form of AEG-1 (S298D), to construct AAV-AEG-1 (S298D), and to apply an animal model for Parkinson's disease. As a result, it was confirmed that it exhibits a protective effect on brain tissue by preserving dopaminergic neurons and dopamine nerve fibers and thus AEG-1 is useful as a composition for preventing or treating Parkinson's disease, a health food composition for preventing or improving Parkinson's disease, etc.

DESCRIPTION OF DRAWINGS

The patent or application file contains at least one drawing executed in color. Copies of this patent or patent application publication with color drawing(s) will be provided by the Office upon request and payment of the necessary fee.

FIG. 3 shows a result of confirming neuroprotective effects by AEG-1 (S298D) in which 6-OHDA was administered to induce Parkinson's disease 3 weeks after the administration of AAV-AEG-1 (S298D) to the substantia nigra of C57BL/6 mouse, followed by TH staining and cresyl violet staining (A: control midbrain substantia nigra, B: midbrain substantia nigra of mice administered 6-OHDA, C: midbrain substantia nigra of mice administered 6-OHDA 3 weeks after AAV-GFP administration, D: midbrain substantia nigra of mice administered 6-OHDA 3 weeks after AAV-AEG-1 (WT) administration, E: midbrain substantia nigra of mice administered 6-OHDA 3 weeks after AAV-AEG-1 (S298D) administration; a: control cerebral striatum, b: cerebral striatum of mice administered 6-OHDA, c: cerebral striatum of mice administered 6-OHDA 3 weeks after administration of AAV-GFP, d: cerebral striatum of mice administered 6-OHDA 3 weeks after administration of AAV-AEG-1 (WT), e: cerebral striatum of mice administered 6-OHDA 3 weeks after AAV-AEG-1 (S298D) administration; upper scale bar, 200 μm; lower scale bar, 1000 μm).

BEST MODE

The inventors of the present invention introduced a point mutation in AEG-1 to induce the constitutively active form, AEG-1 (S298D), and constructed AAV-AEG-1 (S298D) and applied it to an animal model of Parkinson's disease and thus confirmed that the dopaminergic neurons and dopamine nerve fibers were preserved, and a sense of balance and motor learning ability and motor activity were improved, and completed the present invention.

Accordingly, the present invention provides AEG-1 S298D mutation protein represented by SEQ ID NO: 1 in which 298th serine (S) from N-terminus in full amino acid sequence of AEG-1 (astrocyte elevated gene-1) protein is substituted by aspartic acid (D).

Also, the present invention provides a gene encoding the AEG-1 S298D mutant protein.

The AEG-1 (astrocyte elevated gene-1) induces thymidylate synthase (TS) and late SV40 factor (LSF/TFCP2) which is a tumor gene involved in DNA biosynthesis, and the LSF/TFCP2 is known to play multiple roles in Alzheimer's, inflammation, allergic reactions and anticancer resistance.

In the present invention, AEG-1 (S298D), a constitutively active form in which a point mutation was introduced into the AEG-1 gene and the 298th serine (S) was substituted by aspartic acid (D) was induced to prepare AAV-AEG-1 (S298D), and as a result of administration to the substantia nigra of C57BL/6 mice, it was expressed in the substantia nigra region and dopaminergic neurons.

In addition, as a result of inducing Parkinson's disease animal model by administering AAV-AEG-1 (S298D) to C57BL/6 mouse substantia nigra, and then administering 6-OHDA, it was confirmed that the AAV-AEG-1 (S298D) preserves dopaminergic neurons and dopamine nerve fibers and improves a sense of balance and motor learning ability.

In addition, as a result of simultaneous administration of AAV/DJ-α-Synuclein (A53T) and AAV-AEG-1 (S298D) to the right midbrain of SD rats, it was confirmed that the AAV-AEG-1 (S298D) can act on the damaged dopamine nervous system to improve motor activity.

As used herein, the term "point mutation" refers to a mutation that occurs after one nucleotide is converted, and refers to preventing or modifying the production of a specific protein in the DNA transcription step. Most of them occur due to incorrect transcription of adenine and guanine, which are the same purine family, or by incorrect transcription of cytosine and thymine, which are the same pyrimidine family, and these point mutations are known to destroy or alter the information of the codon.

In addition, the present invention provides an expression vector containing the gene.

It should be noted that the expression vector may be an adeno-associated virus vector, but it is not limited thereto.

In addition, the present invention provides a pharmaceutical composition for preventing or treating Parkinson's disease comprising the protein, the gene, or the expression vector as an active ingredient.

The composition can prevent or treat Parkinson's disease by preserving dopaminergic neurons and dopamine nerve fibers, and improving a sense of balance and motor learning ability.

When the composition of the present invention is a pharmaceutical composition, for administration, it may include a pharmaceutically acceptable carrier, excipient or diluent in addition to the above-described active ingredients. Examples of the carrier, excipient and diluent include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oils.

The pharmaceutical compositions of the present invention can be formulated and used in the form of oral formulations such as powders, granules, tablets, capsules, suspensions, emulsions, syrups, aerosols, external preparations, suppositories, or sterile injectable solutions according to a conventional method. In detail, when formulated, it may be prepared using diluents or excipients such as fillers, weighting agents, binders, wetting agents, disintegrants and surfactants that are commonly used. Solid preparations for oral administration include tablets, pills, powders, granules, capsules, and the like, but they are not limited thereto. Such a solid preparation may be prepared by mixing at least one excipient, for example, starch, calcium carbonate, sucrose, lactose, gelatin, etc. in addition to the active ingredient. Further, in addition to simple excipients, lubricants such as magnesium stearate and talc may also be used. It can be prepared by adding various excipients such as wetting agents, sweetening agents, fragrances, preservatives, and the like, in addition to liquids and liquid paraffins for oral use. Formulations for parenteral administration include sterile aqueous solutions, non-aqueous solvents, suspensions, emulsions, lyophilized formulations, and suppositories. As the non-aqueous solvent and suspending agent, propylene glycol, polyethylene glycol, vegetable oil such as olive oil, injectable ester such as ethyl oleate, and the like may be used. As a base for suppositories, witepsol, macrosol, Tween 61, cacao butter, laurin, glycerogelatin, and the like may be used.

A suitable dosage of the pharmaceutical composition of the present invention varies depending on the condition and weight of the patient, the severity of the disease, the form of the drug, and the time, but can be appropriately selected by a person skilled in the art. Thus, the daily dosage of the pharmaceutically acceptable salt is preferably 0.001 mg/kg to 50 mg/kg, and may be administered once to several times a day as necessary.

In addition, the present invention provides a health food composition for preventing or improving Parkinson's disease comprising the protein, the gene, or the expression vector as an active ingredient.

The health functional food composition may contain various nutrients, vitamins, minerals (electrolytes), flavors such as synthetic flavors and natural flavors, etc., colorants and fillers (cheese, chocolate etc.), pectic acid and its salts, alginic acid and its salts, organic acids, protective colloid thickeners, pH adjusting agents, stabilizers, preservatives, glycerin, alcohols, carbonating agents used in carbonated drinks, and the like. It may also contain flesh for the production of natural fruit juices, synthetic fruit juices and vegetable drinks. These components may be used independently or in combination. In addition, the health functional food composition may be in the form of any one of meat, sausage, bread, chocolate, candy, snack, confectionery, pizza, ramen, gum, ice cream, soup, beverage, tea, functional water, drink, alcohol and vitamin complex.

In addition, the health functional food composition may further include a food additive and compliance as a food additive is determined by the standards for the applicable item in accordance with General Regulations and General Test Methods of Korean Food Additives Codex approved by the Ministry of Food and Drug Safety, unless otherwise provided.

Examples of the items published in the above-mentioned "Korean Food Additives Codex" include chemical synthetics such as ketones, glycine, potassium citrate, nicotinic acid, and cinnamic acid and the like, natural additives such as persimmon color, licorice extract, crystalline cellulose, kaoliang color and guar gum and the like, mixed preparations such as L-sodiumglutamate preparation, alkaline agents for noodles, preservative formulation and a tar color formulation and the like.

At this time, the content of the composition according to the present invention added to food in the process of manufacturing the health food composition may be appropriately added or subtracted as needed.

MODE FOR INVENTION

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

Example 1: Preparation of AAV-AEG-1 (S298D)

1-1. Preparation of pBL-AEG-1(S298D) Recombinant Vector

Figure 1:
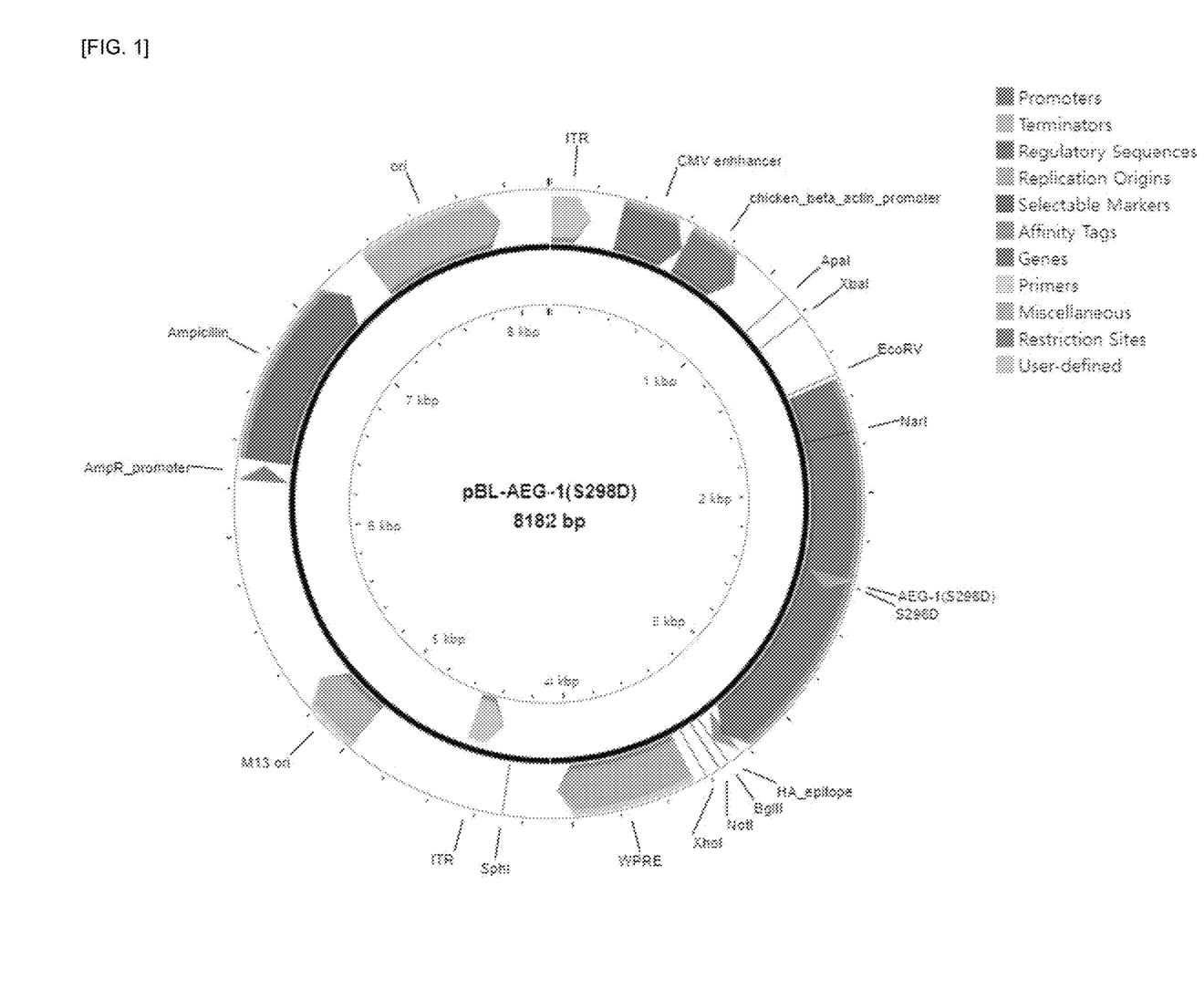
FIG. 1 shows a vector map of pBL-AEG-1(S298D)-HA.

A pBL-AEG-1 (S298D) recombinant vector into which the AEG-1 (S298D) gene was introduced was prepared by introducing the AEG-1 (astrocyte elevate gene-1) (S298D) gene into the pBL plasmid (HA-tag), and its vector map is shown in FIG. 1.

1-2. Preparation of AAV-AEG-1 (S298D)

AAV (adeno-associated virus)-AEG-1 (S298D) was produced by requesting the University of North Carolina Vector Core and the genetic titer was $3.7 \times 10^{12}$ viral genomes/ml. Green fluorescent protein (GFP) or wild-type AEG-1 activated in the same viral backbone was subcloned and used as a control.

Example 2: Analysis of Effect of AEG-1 (S298D) in Parkinson's Disease Animal Model 2-1. Experimental Animal and AAV-AEG-1 (S298D) Administration 8-week-old male C57BL/6 mice or SD rats (Sprague-Dawley rats) were purchased from Daehan Biolink (Eumseong, Korea). A mixture of ketamine (115 mg/kg, Yuhan) and rompun (23 mg/kg, Bayer Korea Ltd.) was administered intraperitoneally (IP) to each mouse or rat to anesthetize it, and it was placed on a stereotaxic frame (David Kopf Instrument, Tujunga, Calif., USA). According to a known experimental method (Paxinos and Watson, 1998), using a 10 µl Hamilton syringe (30S needle) to which a syringe pump (KD Scientific, NewHope, PA) is attached, AAV-AEG-1 (S298D) was injected into the right region of midbrain substantia nigra (SN) of each mouse [(anterior-posterior (AP): 0.35 cm; ML (medial-lateral): +0.11 cm; DV (dorsal-ventral): 0.37 cm, relative to bregma] or midbrain substantia nigra of rats [AP: −0.60 cm; ML: −0.23 cm; DV: −0.76 cm, relative to bregma].

After administration, the needle was held for an additional 5 minutes before slowly withdrawing. At this time, 2 µl of the viral vector suspension was administered for 20 minutes at a rate of 0.1 µl/min.

2-2. Immunohistochemical Staining

Immunohistochemical staining was performed by modifying a known experimental method (Kim et al., 2011; Kim et al., 2012; Leem et al., 2018). After transcardial perfusion was performed on each mouse, the tissue was fixed, and the brain tissue was sectioned at a thickness of 30 µm. After washing the tissue section with PBS, it was incubated with the primary antibody for 48 hours at room temperature. Rabbit anti-tyrosine hydroxylase (TH, 1:2000; Pel-Freez, Brown Beer, Wis.) and mouse anti-HA (1:100; Cell-signaling, Beverly, MA) were used as primary antibodies. After incubation, the tissue sections were washed again with PBS and then incubated with a secondary antibody, and treated with an avidin-biotin complex kit (Vector Laboratories, Burlingame, CA) reagent. The tissue sections were incubated with 0.1 M phosphate buffer (PB, containing 0.003% $H_2O_2$) containing 0.5 mg/ml 3,3'-diaminobenzidine (Sigma, St. Louis, MO) and the signal was detected. The stained sample was analyzed using a bright-field microscope (Carl Zeiss, Gφttingen, Germany).

In addition, brain tissue sections were washed with PBS and then incubated with primary antibodies overnight for immunofluorescence labeling. Rabbit anti-tyrosine hydroxylase (TH, 1:2000; Pel-Freez, Brown Beer, WI) and mouse anti-HA (1:100; Cell-signaling, Beverly, MA) were used as primary antibodies. The next day, tissue sections were washed again with PBS and then incubated together with Texas Red conjugated anti-rabbit IgG (1:400; Vector Laboratories) and FITC-conjugated anti-rabbit IgG (1:200; Jackson ImmunoResearch, West Grove, PA) for 1 hour and washed again. It was mounted with Vectashield mounting medium (Vector Laboratories). The stained sample was analyzed using a fluorescence microscope (LSM700, Carl Zeiss, Germany).

Figure 2:
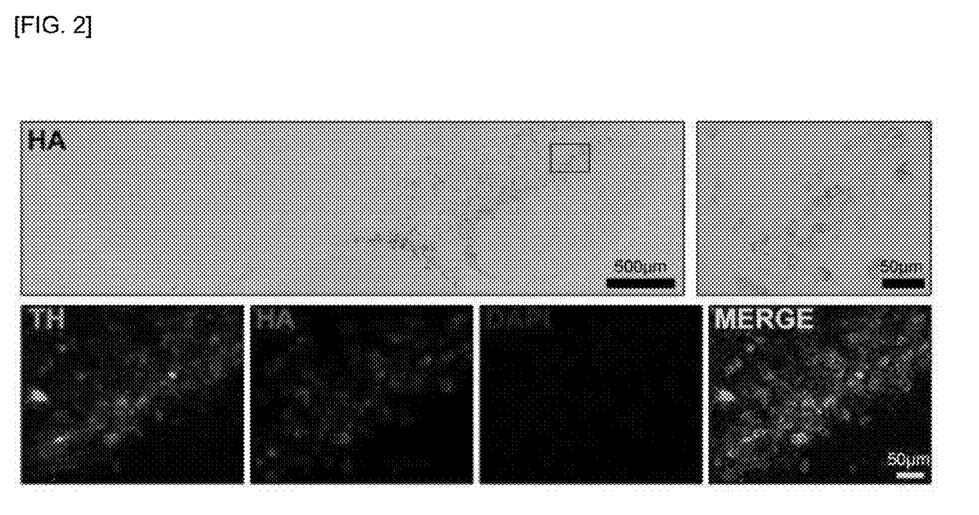
FIG. 2 shows a result of staining brain tissue with HA-tag (left scale bar, 500 μm; right scale bar, 50 μm) or double fluorescence staining with HA-tag and dopaminergic neurons (TH) (Scale bar, 50 μm) 3 weeks after administration of AAV-AEG-1(S298D)-HA(HA-tag) to the substantia nigra of C57BL/6 mouse.

As a result, as shown in FIG. 2, it was confirmed through HA-tag staining that AAV-AEG-1 (S298D) was expressed in the substantia nigra region (SNpc) to which AAV-AEG-1 (S298D) was administered (FIG. 2), it was confirmed that the AEG-1 (S298D) gene (HA-tag, green) was expressed in dopaminergic neurons [tyrosine hydroxylase (TH)-positive cells, red] (FIG. 2, below).

2-3. 6-OHDA Lesion

As in Example 2-1, to prevent non-specific absorption of 6-hydroxydopamine (6-OHDA) desipramine (25 mg/kg, Sigma, St. Louis, MO.) was pretreated 3 weeks after administration of AAV-AEG-1 (S298D) to each mouse substantia nigra. Each mouse was anesthetized by administering a mixture of ketamine (115 mg/kg) and rompun (23 mg/kg) intraperitoneally (i.p), and then placed in a stereotaxic frame. Then, Parkinson's disease was induced by administering a 6-OHDA solution (5.0 μg/μl in 0.9% NaCl/0.02% ascorbate) at a concentration of 15 μg/3 μl at a rate of 0.5 μl/min using a microliter syringe. Administration was performed on the right striatum (AP: +0.09 cm; ML: +0.22 cm; DV: 0.25 cm relative to bregma). After administration, the needle was held for an additional 5 minutes before slowly withdrawing. After separating the brain tissue from each mouse, TH staining was performed in the same manner as in Example 2-2. In addition, for Nissl staining, an SN tissue sample was mounted on a gelatin-coated slide and stained with 0.5% cresyl violet (Sigma). Then, the analysis was performed using a bright field microscope.

Figure 3:
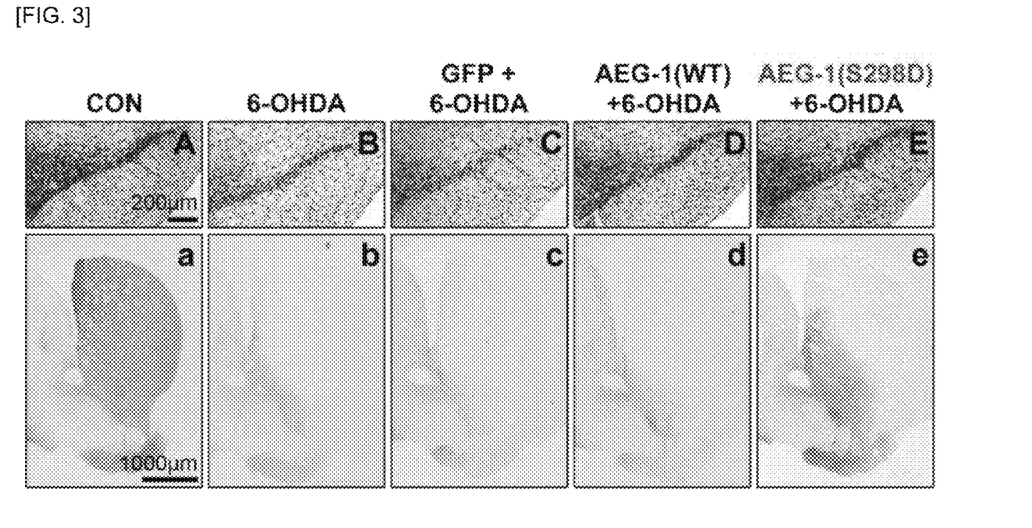

As a result, as shown in FIG. 3, it was confirmed that relatively more dopaminergic neurons (brown) remained in mice administered 6-OHDA 3 weeks after the administration of AEG-1 (S298D) (E) compared to mice administered with only the neurotoxic substance 6-OHDA (B) or mice administered with 6-OHDA 3 weeks after administration of GFP (C) or mice administered with 6-OHDA 3 weeks after administration of AEG-1 (WT) (D) and the size of the remaining dopaminergic neurons was also preserved.

In addition, it was confirmed that relatively more dopamine nerve fibers (brown) remained in mice to which 6-OHDA was administered 3 weeks after the administration of AEG-1 (S298D) (e) compared to mice administered only the neurotoxic substance 6-OHDA (b) or mice administered 6-OHDA 3 weeks after administration of GFP (c) or mice administered 6-OHDA 3 weeks after administration of AEG-1 (WT) (d).

2-4. Rota-Rod Test

Rota-rod test was performed by modifying a known experimental method (Kim et al., 2016; Leem et al., 2018). Each mouse was trained to adapt to a rotating axis at a speed of 10 rpm for 10 minutes once a day from 3 days before administration of 6-OHDA. Each mouse was placed on a shaft accelerating at 4-40 rpm for 5 minutes twice a day from the 5th to the 7th day of 6-OHDA administration, and the time point of falling off the shaft was measured to evaluate the motor performance of each mouse. The values obtained through the experiment performed for a total of 3 days were used to calculate the average value of the time each mouse fell off the shaft, and the average time each mouse fell off the axis was used to calculate the average time to deviate from each group.

Figure 4:
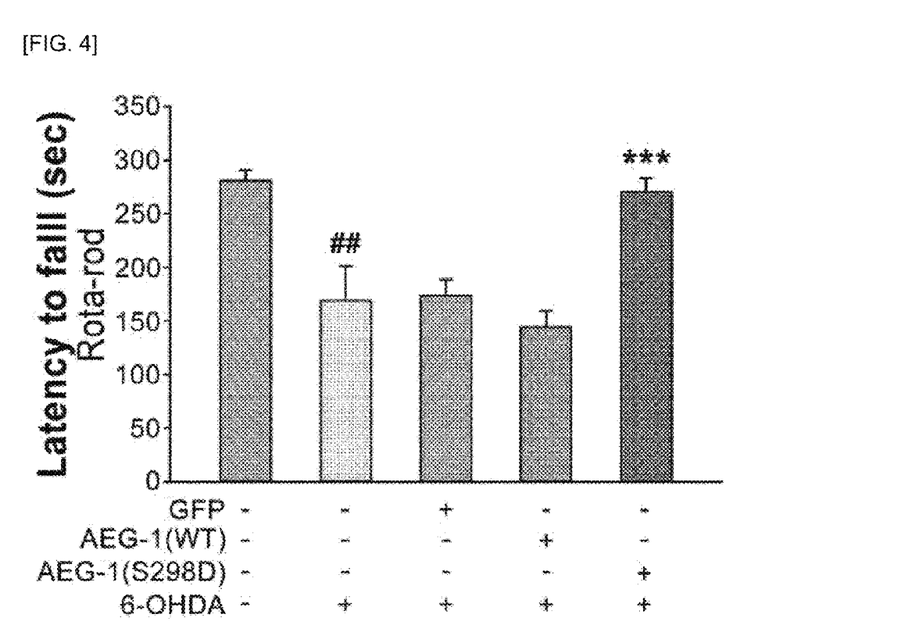
FIG. 4 shows a result of confirming a sense of balance and motor learning ability by AEG-1 (S298D) by Rota-rod test in which 6-OHDA is administered to induce Parkinson's disease 3 weeks after the administration of AAV-AEG-1 (S298D) to the substantia nigra of C57BL/6 mouse (unit: second).

As a result, as shown in FIG. 4, it was confirmed that mice administered with 6-OHDA 3 weeks after the administration of AEG-1 (S298D) stayed on the shaft for a longer period of time compared to mice administered with only the neurotoxic substance, 6-OHDA or mice administered with 6-OHDA 3 weeks after administration of GFP or mice administered 6-OHDA 3 weeks after administration of AEG-1 (WT). The time that 6-OHDA-injected mice 3 weeks after administration of AEG-1(S298D) stayed on the shaft was similar to the time that the normal control mice stayed on the shaft.

2-5. α-Synuclein Lesion

In animal models, the accumulation of α-Synuclein induces a decrease in motor activity, and thus the accumulation of α-Synuclein in the right brain decreases the motility of the left frontal head, resulting in asymmetric motility.

Accordingly, in order to analyze motor activity in the Parkinson's disease animal model, AAV/DJ-α-Synuclein (A53T) was injected into the right midbrain substantia nigra of each rat in the same manner as in Example 2-1. AAV/DJ-EGFP was used as a virus control.

2-6. Cylinder Test

A cylinder test was performed by modifying a known experimental method (Won et al., 2016). Twelve weeks after virus injection, the rat was placed in a cylindrical transparent glass tube with a diameter of 30 cm and a height of 50 cm, and motor activity of the left and right forefoot was evaluated for 5 minutes. When the total number of contact with the glass wall of the left and right forefoot was 20 times, the ratio of the number of contact with the right forefoot and the number of contact with the left forefoot was calculated by the following equation.

((number of right forefoot contact percentage)−
(number of left forefoot contact percentage))/
((number of right forefoot contact percentage)+
(number of left forefoot contact percentage))×
100     [Calculation Equation 1]

Figure 5:
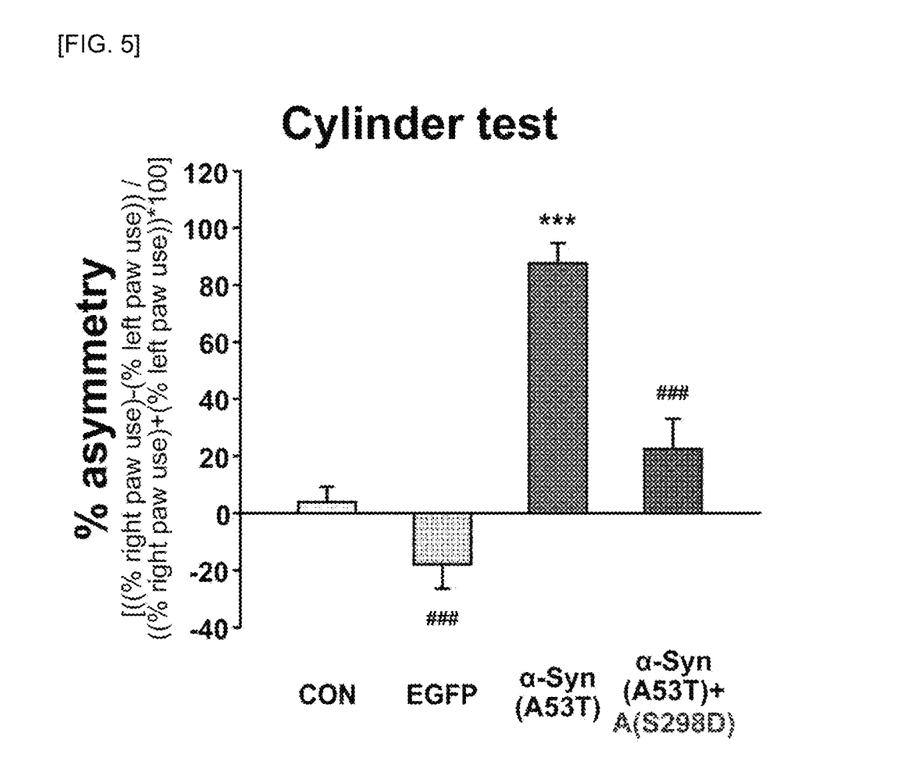
FIG. 5 shows a result of confirming the motor activity ability by cylinder test 12 weeks after simultaneous administration of AAV/DJ-α-Synuclein (A53T) and AAV-AEG-1 (S298D) to the right midbrain substantia nigra of SD rats (unit: number of times).

As a result, as shown in FIG. 5, in the normal control (CON) rat, the motor activity of the left and right forefoot was similar to each other and the asymmetry was significantly low, but in rats to which α-Synuclein (A53T) was administered alone, the activity of the left forefoot decreased and asymmetry was observed very high as the activity of the right forefoot was concentrated. In addition, in rats administered with α-Synuclein (A53T) and AEG-1 (S298D), it was confirmed that the activities of the left forefoot and the right forefoot were similar, indicating a mobility close to symmetry. It was also confirmed that the motor activities of the left and right forefoot were close to symmetry even in the rats administered with EGFP as a virus control group.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The scope of the present invention is indicated by the claims to be described later, and all changes or modified forms derived from the meaning and scope of the claims and their equivalent concepts should be construed as being included in the scope of the present invention.

The invention claimed is:

1. A method of treating Parkinson's disease in a subject in need thereof, comprising:

providing a pharmaceutical composition comprising a gene encoding AEG-1 (astrocyte elevated gene-1) S298D mutant protein of SEQ ID NO: 1, or an expression vector comprising the gene encoding the AEG-1 S298D mutant protein of SEQ ID NO: 1; and administering the pharmaceutical composition to the subject, wherein the subject is a mouse or rat with Parkinson's disease induced by administration of 6-OHDA or AAV/DJ-α-synuclein (A53T), and the pharmaceutical composition preserves dopaminergic neurons and dopamine nerve fibers, and improves sense of balance and motor learning ability more than a wild-type AEG-1 such that the Parkinson's disease is treated.

2. The method of claim 1, wherein the gene consists of SEQ ID NO: 2.

* * * * *

SEQUENCE LISTING

<160> NUMBER OF SEQ ID NOS: 2

<210> SEQ ID NO 1
<211> LENGTH: 582
<212> TYPE: PRT
<213> ORGANISM: Homo sapiens

<400> SEQUENCE: 1

Met Ala Ala Arg Ser Trp Gln Asp Glu Leu Ala Gln Gln Ala Glu Glu
1               5                   10                  15

Gly Ser Ala Arg Leu Arg Glu Met Leu Ser Val Gly Leu Gly Phe Leu
            20                  25                  30

Arg Thr Glu Leu Gly Leu Asp Leu Gly Leu Glu Pro Lys Arg Tyr Pro
        35                  40                  45

Gly Trp Val Ile Leu Val Gly Thr Gly Ala Leu Gly Leu Leu Leu Leu
    50                  55                  60

Phe Leu Leu Gly Tyr Gly Trp Ala Ala Ala Cys Ala Gly Ala Arg Lys
65                  70                  75                  80

Lys Arg Arg Ser Pro Pro Arg Lys Arg Glu Glu Ala Ala Val Pro
                85                  90                  95

Ala Ala Ala Pro Asp Asp Leu Ala Leu Leu Lys Asn Leu Arg Ser Glu
            100                 105                 110

Glu Gln Lys Lys Lys Asn Arg Lys Lys Leu Ser Glu Lys Pro Lys Pro
            115                 120                 125

Asn Gly Arg Thr Val Glu Val Ala Glu Gly Ala Val Arg Thr Pro
        130                 135                 140

Gln Ser Val Thr Ala Lys Gln Pro Pro Glu Ile Asp Lys Lys Asn Glu
145                 150                 155                 160

Lys Ser Lys Lys Asn Lys Lys Ser Lys Ser Asp Ala Lys Ala Val
                165                 170                 175

Gln Asn Ser Ser Arg His Asp Gly Lys Glu Val Asp Gly Ala Trp
            180                 185                 190

Glu Thr Lys Ile Ser His Arg Glu Lys Arg Gln Gln Arg Lys Arg Asp
            195                 200                 205

Lys Val Leu Thr Asp Ser Gly Ser Leu Asp Ser Thr Ile Pro Gly Ile
        210                 215                 220

Glu Asn Thr Ile Thr Val Thr Thr Glu Gln Leu Thr Thr Ala Ser Phe
225                 230                 235                 240

Pro Val Gly Ser Lys Lys Asn Lys Gly Asp Ser His Leu Asn Val Gln
                245                 250                 255

Val Ser Asn Phe Lys Ser Gly Lys Gly Asp Ser Thr Leu Gln Val Ser
            260                 265                 270

Ser Gly Leu Asn Glu Asn Leu Thr Val Asn Gly Gly Trp Asn Glu
        275                 280                 285

Lys Ser Val Lys Leu Ser Ser Gln Ile Asp Ala Gly Glu Glu Lys Trp
            290                 295                 300

Asn Ser Val Ser Pro Ala Ser Ala Gly Lys Arg Lys Thr Glu Pro Ser
305                 310                 315                 320

Ala Trp Ser Gln Asp Thr Gly Asp Ala Asn Thr Asn Gly Lys Asp Trp
                325                 330                 335

Gly Arg Ser Trp Ser Asp Arg Ser Ile Phe Ser Gly Ile Gly Ser Thr
            340                 345                 350

Ala Glu Pro Val Ser Gln Ser Thr Ser Asp Tyr Gln Trp Asp Val
        355                 360                 365

```
Ser Arg Asn Gln Pro Tyr Ile Asp Asp Glu Trp Ser Gly Leu Asn Gly
    370                 375                 380

Leu Ser Ser Ala Asp Pro Asn Ser Asp Trp Asn Ala Pro Ala Glu Glu
385                 390                 395                 400

Trp Gly Asn Trp Val Asp Glu Glu Arg Ala Ser Leu Leu Lys Ser Gln
                405                 410                 415

Glu Pro Ile Pro Asp Asp Gln Lys Val Ser Asp Asp Lys Glu Lys
            420                 425                 430

Gly Glu Gly Ala Leu Pro Thr Gly Lys Ser Lys Lys Lys Lys Lys
        435                 440                 445

Lys Lys Lys Gln Gly Glu Asp Asn Ser Thr Ala Gln Asp Thr Glu Glu
    450                 455                 460

Leu Glu Lys Glu Ile Arg Glu Asp Leu Pro Val Asn Thr Ser Lys Thr
465                 470                 475                 480

Arg Pro Lys Gln Glu Lys Ala Phe Ser Leu Lys Thr Ile Ser Thr Ser
                485                 490                 495

Asp Pro Ala Glu Val Leu Val Lys Asn Ser Gln Pro Ile Lys Thr Leu
            500                 505                 510

Pro Pro Ala Thr Ser Thr Glu Pro Ser Val Ile Leu Ser Lys Ser Asp
        515                 520                 525

Ser Asp Lys Ser Ser Ser Gln Val Pro Pro Ile Leu Gln Glu Thr Asp
    530                 535                 540

Lys Ser Lys Ser Asn Thr Lys Gln Asn Ser Val Pro Pro Ser Gln Thr
545                 550                 555                 560

Lys Ser Glu Thr Ser Trp Glu Ser Pro Lys Gln Ile Lys Lys Lys
                565                 570                 575

Lys Ala Arg Arg Glu Thr
            580

<210> SEQ ID NO 2
<211> LENGTH: 1746
<212> TYPE: DNA
<213> ORGANISM: Homo sapiens

<400> SEQUENCE: 2
atggctgcac ggagctggca ggacgagctg gcccagcagg ccgaggaggg ctcggcccgg      60
ctgcgggaaa tgctctcggt cggcctaggc tttctgcgca ccgagctggg cctcgatctg     120
gggctggagc cgaaacggta ccccggctgg gtgatcctgg tgggcactgg cgcgctcggg     180
ctgctgctgc tgtttctgct gggctacggc tgggccgcgg cttgcgccgg cgcccgcaaa     240
aagcggagga gcccgccccg caagcgggag gaggcggcgg ccgtgccggc cgcggccccc     300
gacgacctgg ccttgctgaa gaatctccgg agcgaggaac aaaagaagaa gaaccggaag     360
aaactgtccg agaagcccaa accaaatggg cggactgttg aagtggctga gggtgaagct     420
gttcgaacac tcaaagtgt aacagcaaag cagccaccag agattgacaa gaaaaatgaa     480
aagtcaaaga aaaataagaa gaaatcaaag tcagatgcta agcagtgca aaacagttca     540 cgccatgatg gaaggaagt tgatgaagga gcctgggaaa ctaaaattag tcacagagag     600
aaacgacagc agcgtaaacg tgataaggtg ctgactgatt ctggttcatt ggattcaact     660
atccctggga tagaaaatac catcacagtt accaccgagc aacttacaac cgcatcattt     720
cctgttggtt ccaagaagaa taaaggtgat tctcatctaa atgttcaagt tagcaacttt     780
aaatctggaa aaggagattc tacacttcag gtttcttcag gattgaatga aaccctcact     840
gtcaatggag gaggctggaa tgaaaagtct gtaaaactct cctcacagat cgatgcaggt     900
```

```
gaggagaagt ggaactccgt ttcacctgct tctgcaggaa agaggaaaac tgagccatct    960
gcctggagtc aagacactgg agatgctaat acaaatggaa aagactgggg aaggagttgg   1020
agtgaccgtt caatattttc tggcattggg tctactgctg agccagtttc tcagtccacc   1080
acttctgatt atcagtggga tgttagccgt aatcaaccct atatcgatga tgaatggtct   1140
gggttaaatg gtctgtcttc tgctgatccc aactctgatt ggaatgcacc agcagaagag   1200
tggggcaatt gggtagacga agaaagagct tcacttctaa agtcccagga accaattcct   1260
gatgatcaaa aggtctcaga tgatgataaa gaaaagggag agggagctct tccaactggg   1320
aaatccaaaa agaaaaaaaa gaaaagaag aagcaaggtg aagataactc tactgcacag   1380
gacacagaag aattagaaaa agagattaga gaagaccttc cagtgaatac ctctaaaacc   1440
cgtccaaaac aggaaaaagc tttttccttg aagaccataa gcactagtga tccagccgaa   1500
gtactcgtca aaaatagcca gcctatcaag actcttccac ctgctacttc taccgagcca   1560
tctgtaatct tatcaaaaag tgattctgac aagagctctt cccaagtgcc gccaatacta   1620
caagagacag ataaatccaa gtcaaatacc aagcaaaata gtgtgcctcc ttcacagacc   1680
aagtctgaaa ctagctggga atctcccaaa caaataaaaa agaagaaaaa agccagacga   1740
gaaacg                                                             1746
```